United States Patent [19]

Miller

[11] Patent Number: 4,617,159
[45] Date of Patent: Oct. 14, 1986

[54] METHOD OF MOLDING A DENTAL SHADE SAMPLE

[76] Inventor: Lloyd L. Miller, 20 Beaver Rd., Weston, Mass. 02193

[21] Appl. No.: 632,400

[22] Filed: Jul. 19, 1984

[51] Int. Cl.$^4$ .................. A61C 13/107; A61C 13/09; A61C 19/10
[52] U.S. Cl. .................................. 264/16; 249/142; 249/155; 249/161; 249/164; 264/245; 433/203.1
[58] Field of Search ............... 264/16, 19, 20, 245; 249/142, 177, 155, 161, 164

[56] References Cited

U.S. PATENT DOCUMENTS

| | | | |
|---|---|---|---|
| 851,284 | 4/1907 | Flinn | 73/429 |
| 1,181,206 | 5/1916 | Basehore et al. | 73/429 |
| 1,599,085 | 9/1926 | Gibson | 264/20 X |
| 2,249,890 | 7/1941 | Dröge | 264/19 X |
| 2,517,100 | 8/1950 | Erdle | 264/20 |
| 2,839,928 | 6/1958 | Fohrman | 73/429 |
| 3,326,049 | 6/1967 | Eley | 73/429 |
| 3,671,008 | 6/1972 | Villalba, Jr. | 249/155 |
| 3,738,177 | 6/1973 | McShirley | 73/429 |
| 3,840,631 | 10/1974 | Alexander | 264/113 |
| 4,155,964 | 5/1979 | Aronow | 264/19 X |

OTHER PUBLICATIONS

Tylman, Stanley D., *Theory and Practice of Crown and Bridge Prostaesdis*, St. Louis, MO, C. V. Mosby, 1940, p. 483.

Johnston, John F..; George Mumford and Roland W. Dykema, *Modern Practice in Dental Ceramics*, Philadelphia, PA, W. B. Saunders, 1967, pp. 1, 9–11.

*Primary Examiner*—Philip Anderson

[57] ABSTRACT

A mold for preparing a plug suitable for making a dental shade sample having a layer of porcelain material having a known thickness; the mold comprises: a base with a cylinder extending upwardly therefrom; a planar platform surface at the upper end of the cylinder, the cylinder being threaded in a region below the platform surface; and a hollow annular housing defining an internal cylindrical surface sized and cooperatively threaded to engage the cylinder threads. Rotation of the housing relative to the cylinder moves the housing vertically and continuously varies the known depth of the cavity between the housing and the platform surface. By proper positioning of the housing and cylinder a known desired cavity depth is obtained and filled with porcelain-forming material to mold a first shade layer. The housing is rotated to increase the cavity depth by known desired increments for subsequent layers.

3 Claims, 3 Drawing Figures

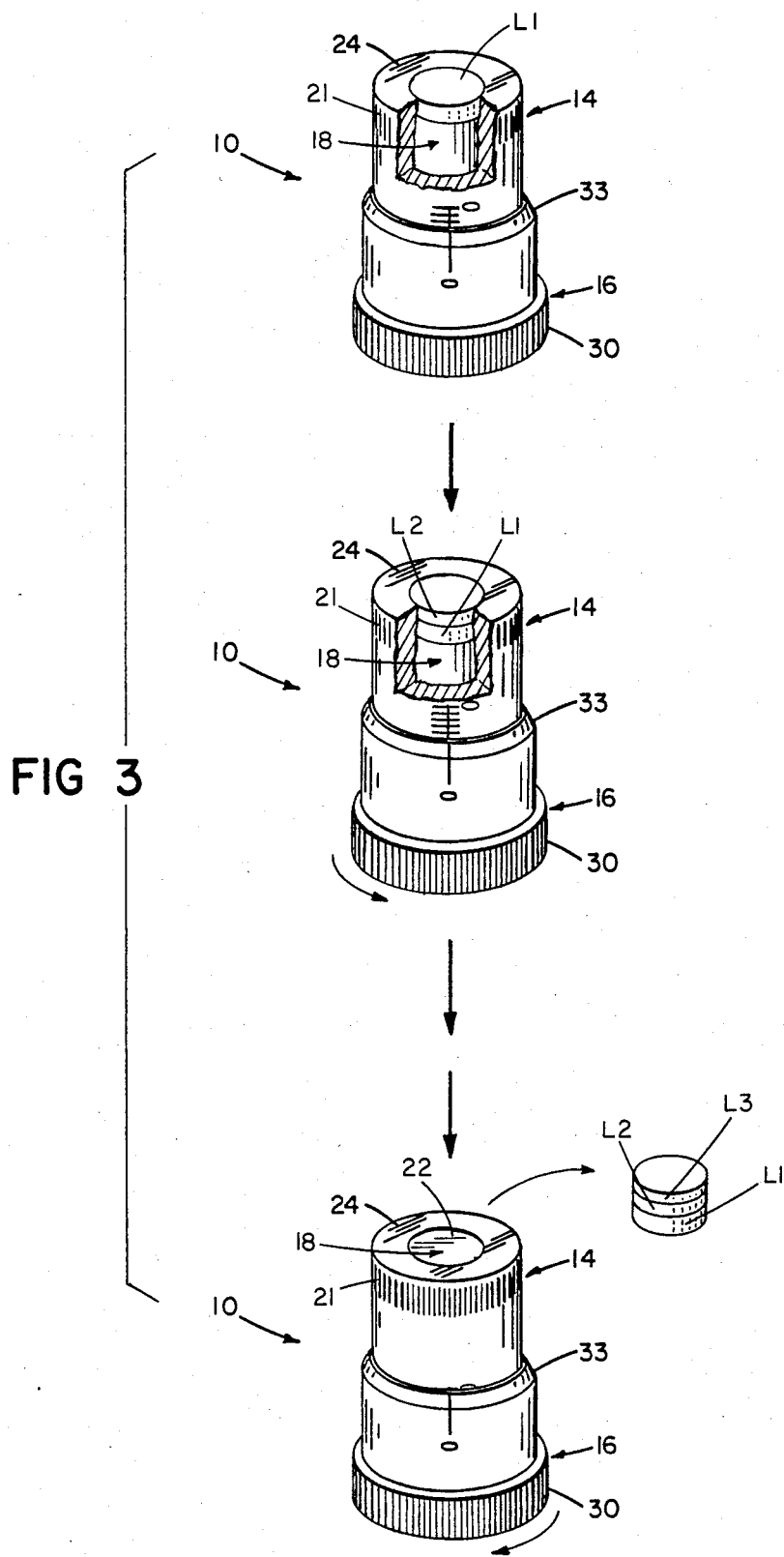

METHOD OF MOLDING A DENTAL SHADE SAMPLE

BACKGROUND OF THE INVENTION

This invention relates to apparatus and methods for making porcelain samples used in selecting external surface characteristics of dental restorations.

In selecting an aesthetically appropriate surface for a specific dental restoration, a shade sample should be very carefully matched to the patient's surrounding teeth. The sample then can be used to obtain a restoration with the appropriate external surface. Such samples are made by firing layers of porcelain powder of precisely known thicknesses to achieve the color hue, value, chroma, and translucence desired. Ordinarily three layers of powder are used. The bottom layer is opaque and the middle and top layer are translucent. The visual qualities of the final shade will depend greatly on the specific thicknesses of the three layers, and those thicknesses must be very carefully controlled.

SUMMARY OF THE INVENTION

The invention features a mold for preparing a plug having one or more layers of porcelain-forming material, each of a known thickness; the plug is used to make a dental shade sample having desired visual characteristics. The mold comprises: a base; a cylinder extending upward from the base; a platform surface at the top of the cylinder, the cylinder being threaded in a region below the platform surface; and a hollow annular housing defining an internal cylindrical surface sized and cooperatively threaded to engage the cylinder threads. In the method of using the mold to make the plug, the housing is rotated to move it vertically with respect to the cylinder to a first position in which a known, desired depth is obtained in the cavity formed by the housing and the platform surface. A porcelain-forming material is inserted in the cavity to that depth. If additional layers are desired, the housing is rotated to a second position to increase the cavity depth by a desired known incremental distance so that a second layer of porcelain-forming material may be added to the cavity to create a second layer of known depth, and so forth for each additional layer.

In preferred embodiments, the plug is removed from the cavity by rotating the housing to raise the platform. The plug has multiple layers. The mold housing has external marks indicative of the depth of the cavity when aligned with a platform mark. The cylinder has a lower threaded portion and an upper unthreaded portion. The mold threads may be either a standard machined thread or they may be calibrated so that rotation of the housing a specific increment, such as 360°, produces a predetermined cavity depth.

The above-described mold and corresponding method enable precise control of the thickness and uniformity of dental shade samples, thus improving the matching of restoration surfaces to surrounding natural teeth. By spacing the cylinder threads from the platform, and by maintaining a tight fit (e.g. with an O-ring) between the housing and the unthreaded portion of the cylinder, porcelain-forming powder is prevented from leaking from the cavity into the threads.

Other features and advantages of the invention will be apparent from the following description of the preferred embodiment and drawings thereof and from the claims.

DESCRIPTION OF THE PREFERRED EMBODIMENT

Figure 1:
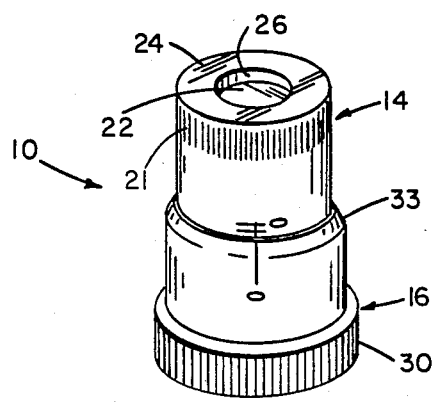
Figure 2:
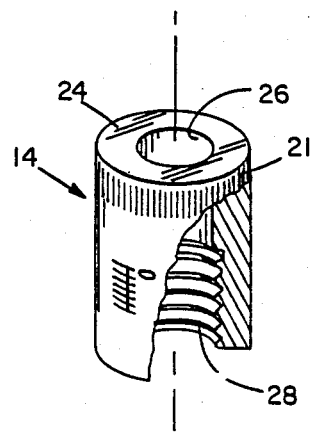
Figure 2:
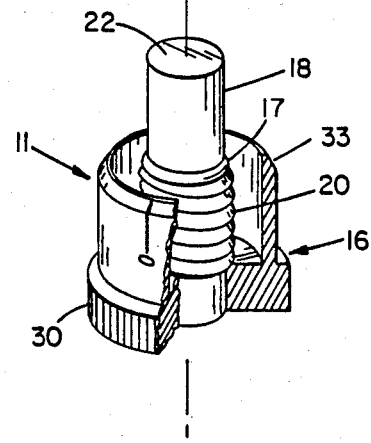

FIG. 1 is a view of a dental shade mold.
FIG. 2 is an exploded view of a modified shade mold.
FIG. 3 is a diagram of steps in a process for making a shade sample.

In FIGS. 1 and 2, dental shade mold 10 is comprised of a lower segment 11 and a housing 14. Lower segment 11 has a horizontal circular base 16 with a ridged surface 30. An elongated cylinder 18 extends upwardly from base 16 and terminates at its upper end in a circular planar platform surface 22. Cylinder 18 has threads 20 around the circumference of its lower portion, but not around the portion adjacent surface 22. A cylindrical sleeve 33 extends upwardly from the circumference of base segment 16.

Housing 14 is a hollow cylindrical member that terminates at its upward end in a horizontal annular surface 24. Along the lower part of its external vertical surface, housing 14 is marked with numerical indicia and corresponding horizontal lines positioned to be exposed as the top of sleeve 33 is lowered by relative rotation of housing 14 and lower segment 11. A vertical line on the external vertical surface of housing 14 is positioned to align with a vertical "O" line on sleeve 33 when surface 22 and surface 24 are aligned. Housing 14 includes threads 28 on the lower portion of its internal vertical surface that cooperate with threads 20. Housing 14 also includes a gripping surface 21 around the top of its outer circumference.

When housing 14 is threaded onto cylinder 18, it may be rotated to move it vertically with respect to cylinder 18. The depth of cavity 26 is thereby varied. A stop may be included in the mating threads to prevent rotation of housing 14 past the point of alignment of the "O" lines, thus preventing extension of surface 22 above the level of surface 24. Cylinder 18 mates very closely to housing 14 to prevent any porcelain-forming powder from getting into the threads and clogging them. Moreover, an O-ring 17 is seated in a groove on cylinder 18 to further seal the threads from cavity 26.

OPERATION

Shade mold 10 is used in the following way to prepare a multi-layered plug suitable for producing a dental shade sample. As shown in FIG. 3 there are three stages of the process of making a plug having three layers designated L1, L2, and L3, respectively:
1. adding the first layer and condensing;
2. adding the second layer and condensing; and, after adding a third layer and condensing,
3. removing the shade mold and baking.

Housing 14 is threaded onto cylinder 18 and rotated to the stop in the threads, at which point surface 22 is flush with housing surface 24, and vertical line on the housing is aligned with the "O" mark.

The housing is then rotated to move it upwardly on cylinder 18 and create a cavity 26. Some of the horizontal lines on housing 14 are exposed as the top of sleeve 33 is moved vertically downward. Numerical indicia corresponding to those exposed lines indicate the depth of cavity 26. With the housing in position to define a cavity of a known desired depth, the cavity is filled with a porcelain-forming powder. To form the first layer L1, the powder is condensed until it fills the cavity and its upper surface is flush with housing surface 24.

Housing 24 is rotated upward to a second position, adding a known desired increment to the depth of cavity 26. A layer L2 of a different porcelain-forming powder is then added to the cavity as described above. The process is repeated to form a third layer L3. The resulting product is a plug having three layers, each a known thickness of a different powder.

The layers may be applied in a desired order. Standardly, the bottom layer is an opaque layer, and the middle and top layers possess varying amounts of translucence. The overall visual effect of the final shade is a function of the materials and thicknesses selected for each of the layers.

The indicia and threaded connection provide continuous control of cavity depth at a known level. The housing can easily be manipulated manually, but the friction between O-ring 17 and the outer surface of cylinder 18 keep the housing in a desired position and prevent undesired movement, e.g., while charging the cavity with powder.

The three-layer plug is carefully removed from the mold by rotating the housing in a direction to drive the cylinder upward in the housing and force the plug out of the cavity. The plug is then fired to form the desired porcelain shade sample having specific thicknesses.

MANUFACTURE

The mold parts may be any suitable heat-resistant material that does not stick to the porcelain-forming powder. Sleeve 33 and base 16 may be aluminum, and cylinder 18 and housing 14 may be stainless steel; the cylinder is then force-fit into a corresponding hole in base 16. The parts may be machined and polished.

OTHER EMBODIMENTS

A polytetrafluoroethylene or nylon cover may be added to the cylinder top to form the platform surface and to ease the removal of the finished plug from the mold; also, the entire upper cylinder may be coated with such a substance to lower the friction between the housing and cylinder, or provide a seal to keep porcelain powder away from cylinder 18. A resilient detent member may be attached to base 16 and biased against the external wall of housing 14 to prevent undesirable movement when the correct rotational position has been achieved. Plugs of more or fewer than 3 layers may be produced using the mold.

I claim:

1. A method of preparing a dental shade sample comprising a plurality of layers, each of a known thickness, said method comprising:
   (1) providing a dental shade sample mold for preparing a plug comprising:
      a base,
      a cylinder extending upwardly from said base,
      a planar platform surface at the upper end of said cylinder, said cylinder being threaded in a region below said platform, and
      a hollow annular housing defining an internal cylindrical surface sized and cooperatively threaded to engage said cylinder threads,
      whereby the position of the housing relative to said cylinder establishes the depth of the cavity defined by said housing surface and said platform, and rotation of said housing relative to said cylinder moves the housing vertically with respect to the cylinder and causes said cavity depth to vary continuously by known amounts;
   (2) positioning said housing and cylinder in a series of positions by causing relative rotation of said housing and cylinder, said cavity having a different, known depth at each said position;
   (3) at each said position, inserting porcelain-forming material into said cavity and condensing said porcelain-forming material to fill the cavity with said material, whereby a porcelain-forming plug is formed comprising a plurality of layers each with a known thickness;
   (4) removing said plug from said mold; and
   (5) baking said plug.

2. The method of claim 1 wherein said housing comprises external marks indicative of the depth of said cavity, and said rotation-causing step comprises rotating said housing relative to said cylinder to a position indicated by said indicia.

3. The method of claim 1 wherein said plug-removing step comprises rotating said housing to raise said platform and thereby to force said plug from said cavity.

* * * * *